US007771143B2

(12) United States Patent
Bharadwaj et al.

(10) Patent No.: US 7,771,143 B2
(45) Date of Patent: Aug. 10, 2010

(54) DRILL BIT ASSEMBLY WITH ADJUSTABLE DRILL STOP SLEEVE

(75) Inventors: Jeetendra Bharadwaj, Memphis, TN (US); Carlos E. Gil, Collierville, TN (US); Eric D. Weeks, Millington, TN (US)

(73) Assignee: Warsaw Orthopedic, Inc

(*) Notice: Subject to any disclaimer, the term of this patent is extended or adjusted under 35 U.S.C. 154(b) by 851 days.

(21) Appl. No.: 11/367,551

(22) Filed: Mar. 3, 2006

(65) Prior Publication Data

US 2007/0206996 A1 Sep. 6, 2007

(51) Int. Cl.
*B23B 35/00* (2006.01)
*B23B 51/00* (2006.01)

(52) U.S. Cl. ....................... 408/1 R; 408/202; 408/226; 606/80; 433/75; 433/165

(58) Field of Classification Search ................. 408/202, 408/226, 110–113, 1 R; 606/80, 96; 433/75, 433/165; *A61B 17/16*
See application file for complete search history.

(56) References Cited

U.S. PATENT DOCUMENTS 1,105,154 A * 7/1914 McMillen ................... 408/202
1,883,713 A * 10/1932 Gray ........................... 279/56
2,529,396 A * 11/1950 Hunt ........................... 279/52
2,794,353 A * 6/1957 Bashlow et al. ............. 408/113
2,823,563 A * 2/1958 Nipken ....................... 408/110
2,833,168 A * 5/1958 Nelson ....................... 408/202
2,915,925 A * 12/1959 Nipken ....................... 408/113
3,263,531 A * 8/1966 Sammons et al. ............. 408/97
3,562,913 A * 2/1971 Saffro ......................... 433/75
3,576,076 A * 4/1971 Weissman ................... 433/165
3,620,637 A * 11/1971 Brown ........................ 408/202
4,019,827 A * 4/1977 Christianson et al. ....... 408/202
4,123,193 A 10/1978 Hill
4,168,131 A 9/1979 Hill
4,710,075 A 12/1987 Davison
5,078,552 A 1/1992 Albel
5,382,120 A 1/1995 Parsons
5,690,451 A 11/1997 Thurler et al.
5,795,110 A 8/1998 Wirth, Jr. et al.
5,882,151 A 3/1999 Wirth, Jr. et al.
5,890,897 A * 4/1999 Kruger et al. ................. 433/75
5,957,634 A * 9/1999 Carpinetti ................... 408/226
6,514,258 B1 2/2003 Brown et al.
6,854,938 B2 2/2005 Kopras et al.
6,951,562 B2 * 10/2005 Zwirnmann .................. 606/80
7,163,542 B2 * 1/2007 Ryan ........................... 606/96
7,210,881 B2 * 5/2007 Greenberg .................. 408/202

(Continued)

FOREIGN PATENT DOCUMENTS

DE 2402516 A1 * 7/1975

(Continued)

*Primary Examiner*—Daniel W Howell

(57) ABSTRACT

A drill bit assembly is disclosed and can include a drill bit and a drill stop sleeve disposed around the drill bit. The drill stop sleeve can include a locking collar that can be movable between an unlocked position and a locked position. In the unlocked position, the drill stop sleeve can be movable along the drill bit to one of a plurality of drill stop depths. In the locked position, the drill stop sleeve can be locked along the drill bit in one of the plurality of drill stop depths.

13 Claims, 14 Drawing Sheets

U.S. PATENT DOCUMENTS

| | | | | |
|---|---|---|---|---|
| 2003/0206779 | A1 | 11/2003 | Kopras et al. | |
| 2004/0146367 | A1 | 7/2004 | Gerhardt et al. | |
| 2005/0000732 | A1 | 1/2005 | Geuvers et al. | |
| 2006/0008332 | A1 | 1/2006 | Greenberg et al. | |
| 2006/0184174 | A1 * | 8/2006 | Harris et al. | 606/80 |
| 2007/0099150 | A1 * | 5/2007 | Muller et al. | 433/165 |

FOREIGN PATENT DOCUMENTS

| | | | | |
|---|---|---|---|---|
| DE | 3800482 | A1 | * | 7/1989 |
| DE | 19725401 | C1 | * | 2/1999 |
| DE | 19753574 | A1 | * | 7/1999 |
| GB | 2005572 | A | * | 4/1979 |

* cited by examiner

DRILL BIT ASSEMBLY WITH ADJUSTABLE DRILL STOP SLEEVE

FIELD OF THE DISCLOSURE

The present disclosure relates generally to orthopedics and orthopedic surgery. More specifically, the present disclosure relates to drill bits used to drill into bone tissue.

BACKGROUND

Surgeons typically utilize many tools during orthopedic surgeries. For example, a surgeon may utilize a surgical drill in order to drill into bone tissue, e.g., in order to establish a hole in which a bone screw, a bone nail, or other device, can be inserted. Oftentimes, the depth of such a hole is critical and the surgeon may not want to drill too deep into the bone tissue. As such, it may be necessary to prevent the drill bit from penetrating too deeply into the bone tissue.

DETAILED DESCRIPTION OF THE DRAWINGS

A drill bit assembly is disclosed and can include a drill bit and a drill stop sleeve disposed around the drill bit. The drill stop sleeve can include a locking collar that can be movable between an unlocked position and a locked position. In the unlocked position, the drill stop sleeve can be movable along the drill bit to one of a plurality of drill stop depths. In the locked position, the drill stop sleeve can be locked along the drill bit in one of the plurality of drill stop depths.

In another embodiment, a drill bit is disclosed and can be positioned within a drill stop sleeve. The drill bit can include a plurality of drill stop grooves established therein.

In yet another embodiment, a drill stop sleeve is disclosed and can be positioned around a drill bit. The drill stop sleeve can include a locking arm that can be configured to engage one of a plurality of drill stop grooves established within the drill bit.

In still another embodiment, a method of drilling a hole in an item is disclosed and can include providing a drill bit assembly that includes a drill bit and a drill stop sleeve that can be disposed around the drill bit. Further, the method can include selecting a drill stop depth on a drill bit assembly and locking a drill stop sleeve with respect to a drill bit. The drill stop sleeve can substantially prevent the drill bit from drilling deeper into the item than a selected drill stop depth.

In yet still another embodiment, a kit for field use is disclosed and can include a drill bit assembly that includes a drill bit and a drill stop sleeve that can be disposed around the drill bit. The drill stop sleeve can include a locking collar that can be movable between an unlocked position and a locked position. In the unlocked position, the drill stop sleeve can be moved along the drill bit to one of a plurality of predetermined drill stop depths. Moreover, in the locked position, the drill stop sleeve can be locked along the drill bit in one of the plurality of predetermined drill stop depths. The kit can also include instructions for drilling a hole with the drill bit assembly.

Figure 1:
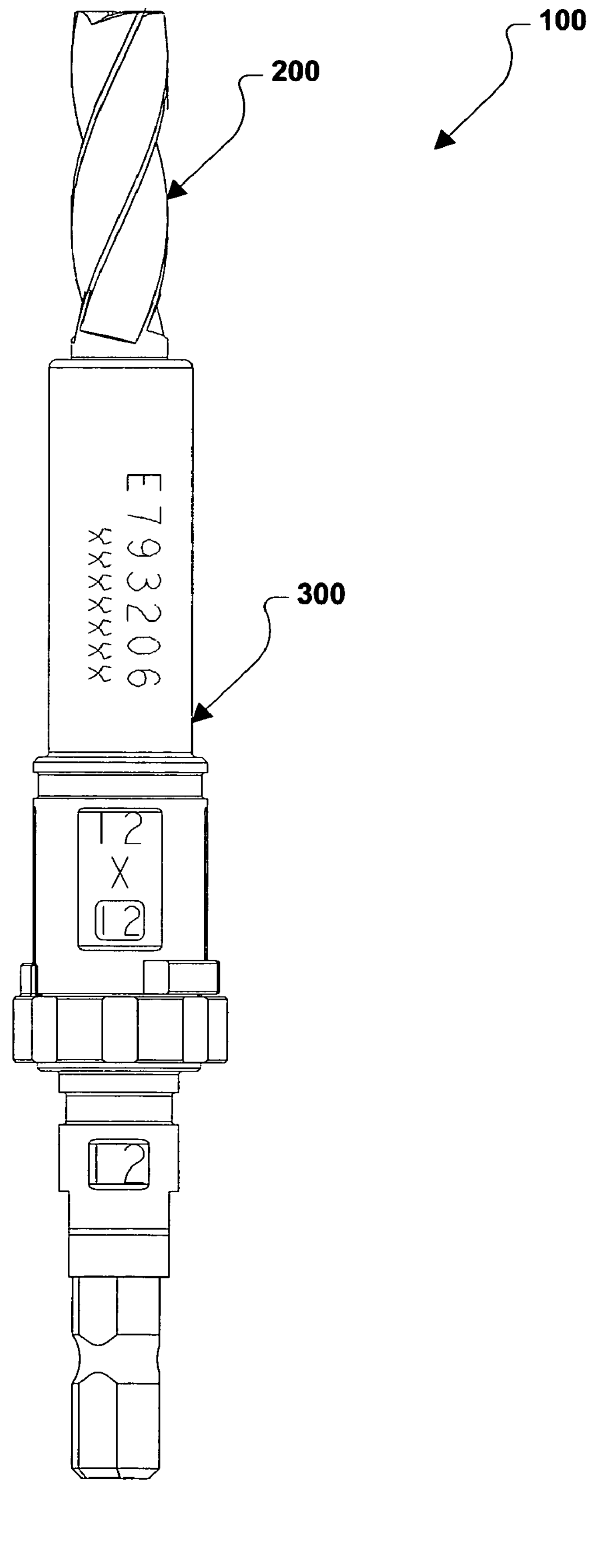
FIG. 1 is a plan view of a drill bit assembly.
Figure 2:
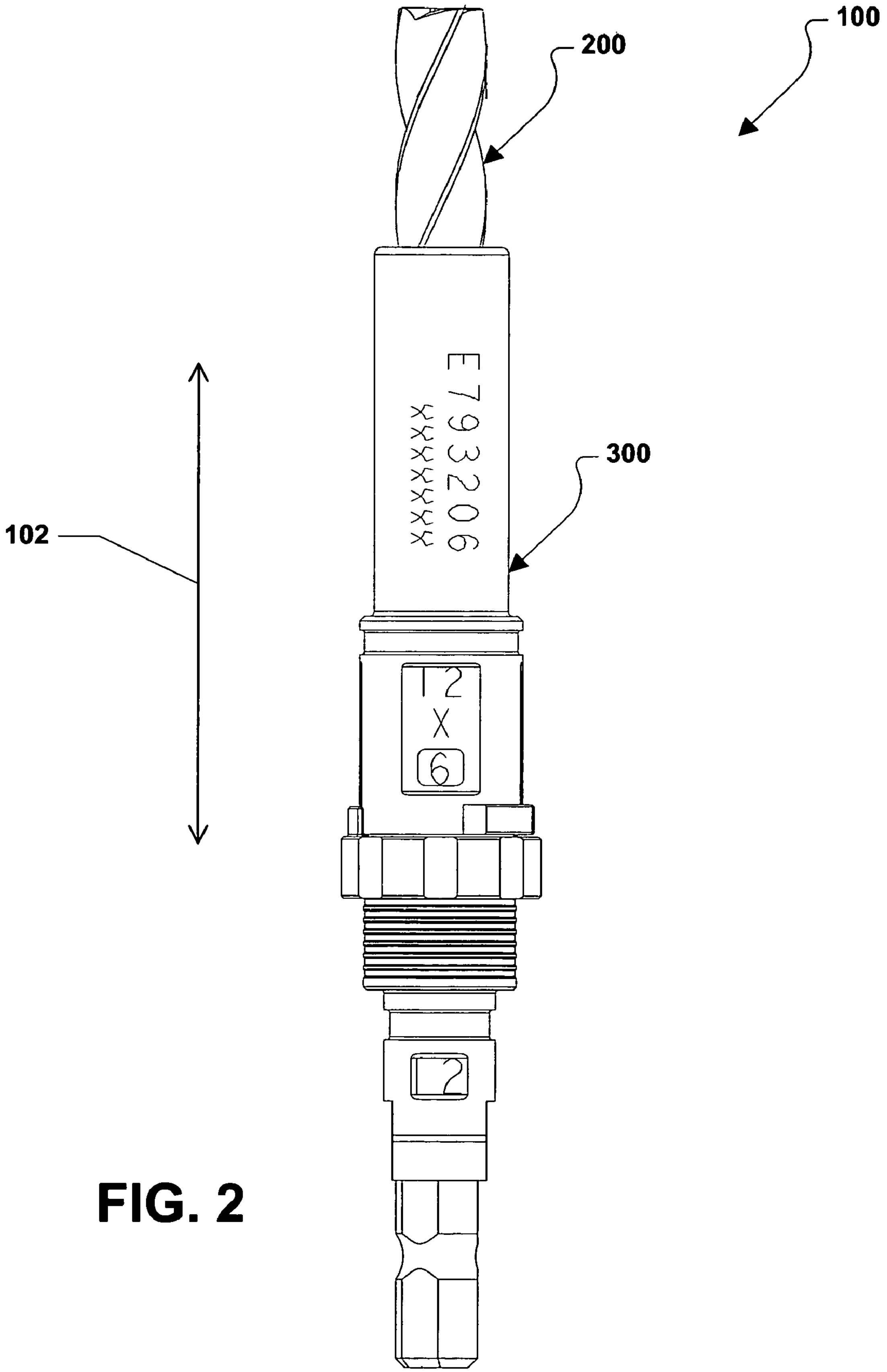
FIG. 2 is another plan view of the drill bit assembly.

Referring initially to FIG. 1, a drill bit assembly is shown and is generally designated 100. As depicted in FIG. 1, the drill bit assembly 100 includes a drill bit 200 and a drill stop sleeve 300 around the drill bit. In a particular embodiment, described in detail below and as indicated by arrow 102 in FIG. 2, the drill stop sleeve 300 can move back and forth between a plurality of positions relative to the drill bit 200. FIG. 1 illustrates the drill bit assembly 100 with the drill stop sleeve 300 in one of the plurality of positions. Moreover, FIG. 2 illustrates the drill bit assembly 100 with the drill stop sleeve 300 in another of the plurality of positions.

Figure 3:
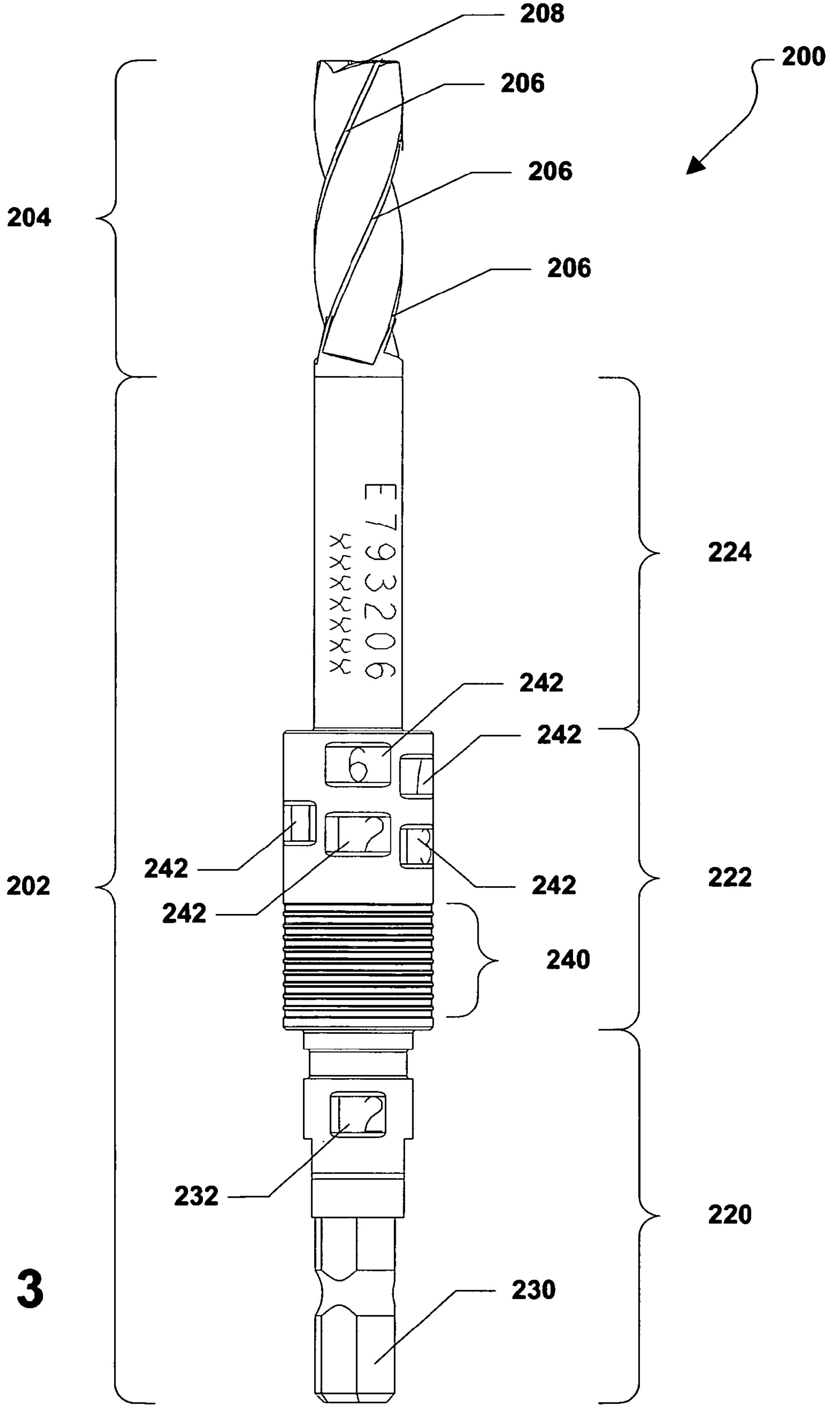
FIG. 3 is a plan view of a drill bit.
Figure 4:
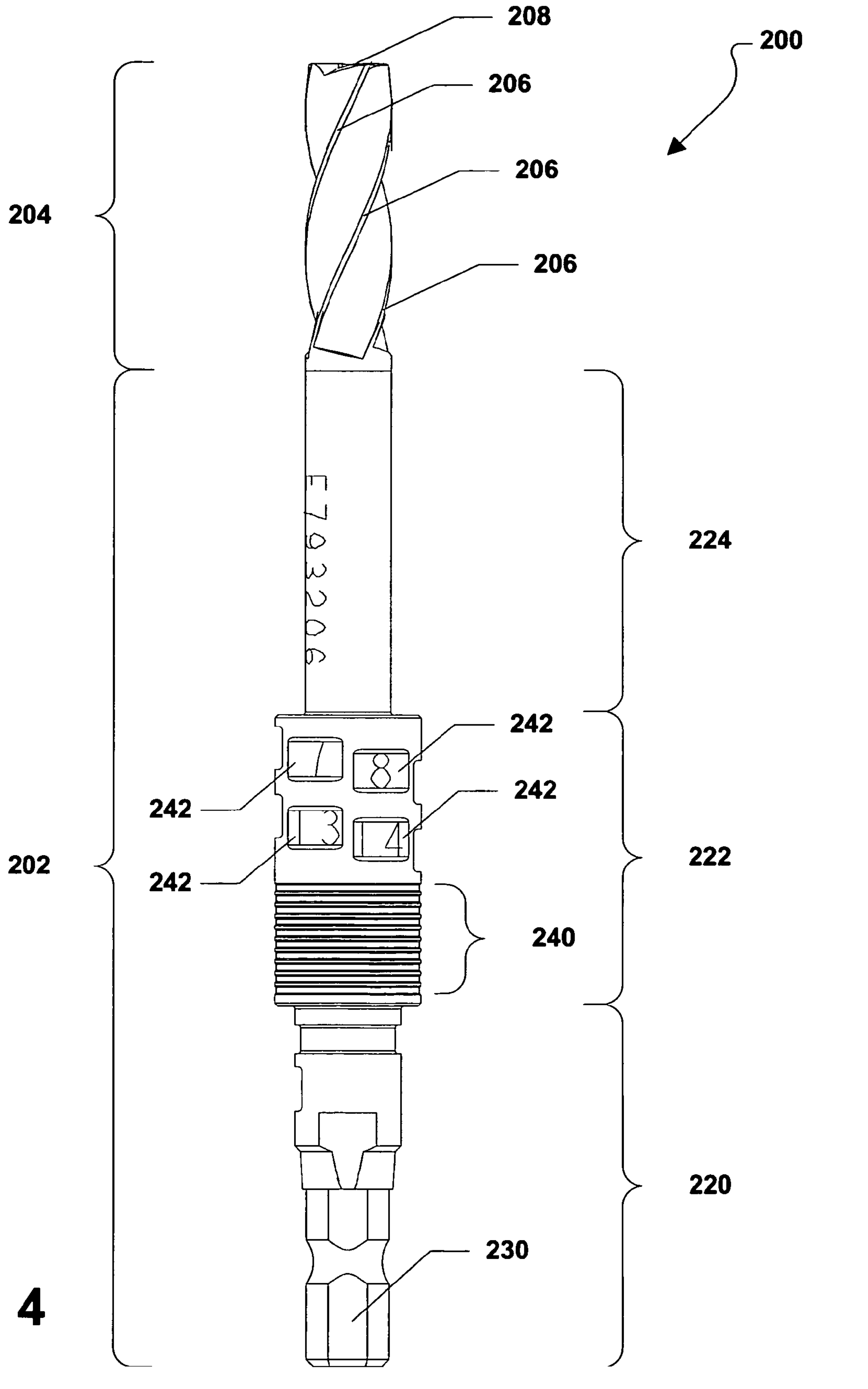
FIG. 4 is another plan view of a drill bit.
Figure 5:
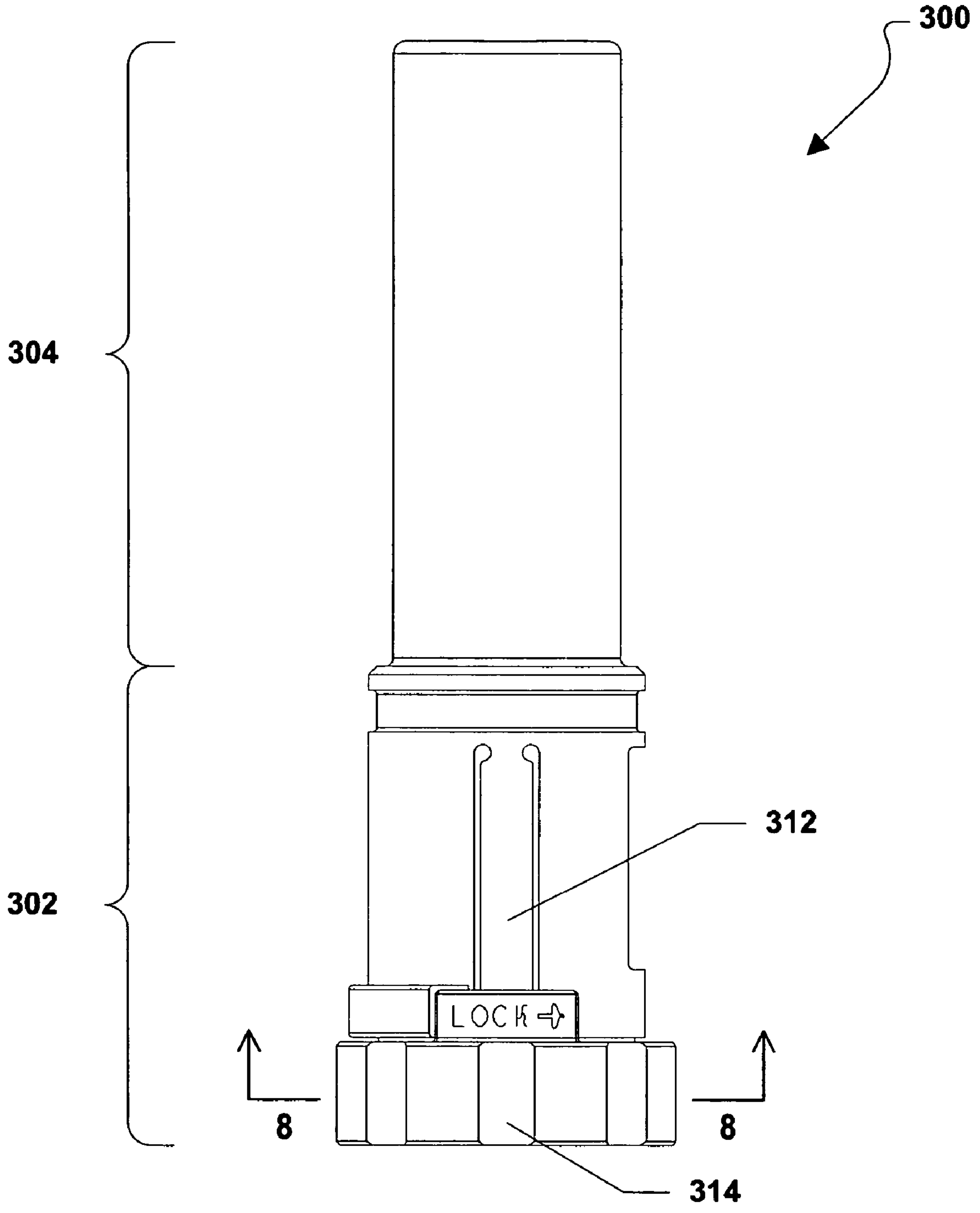
FIG. 5 is a plan view of a drill stop sleeve.
Figure 6:
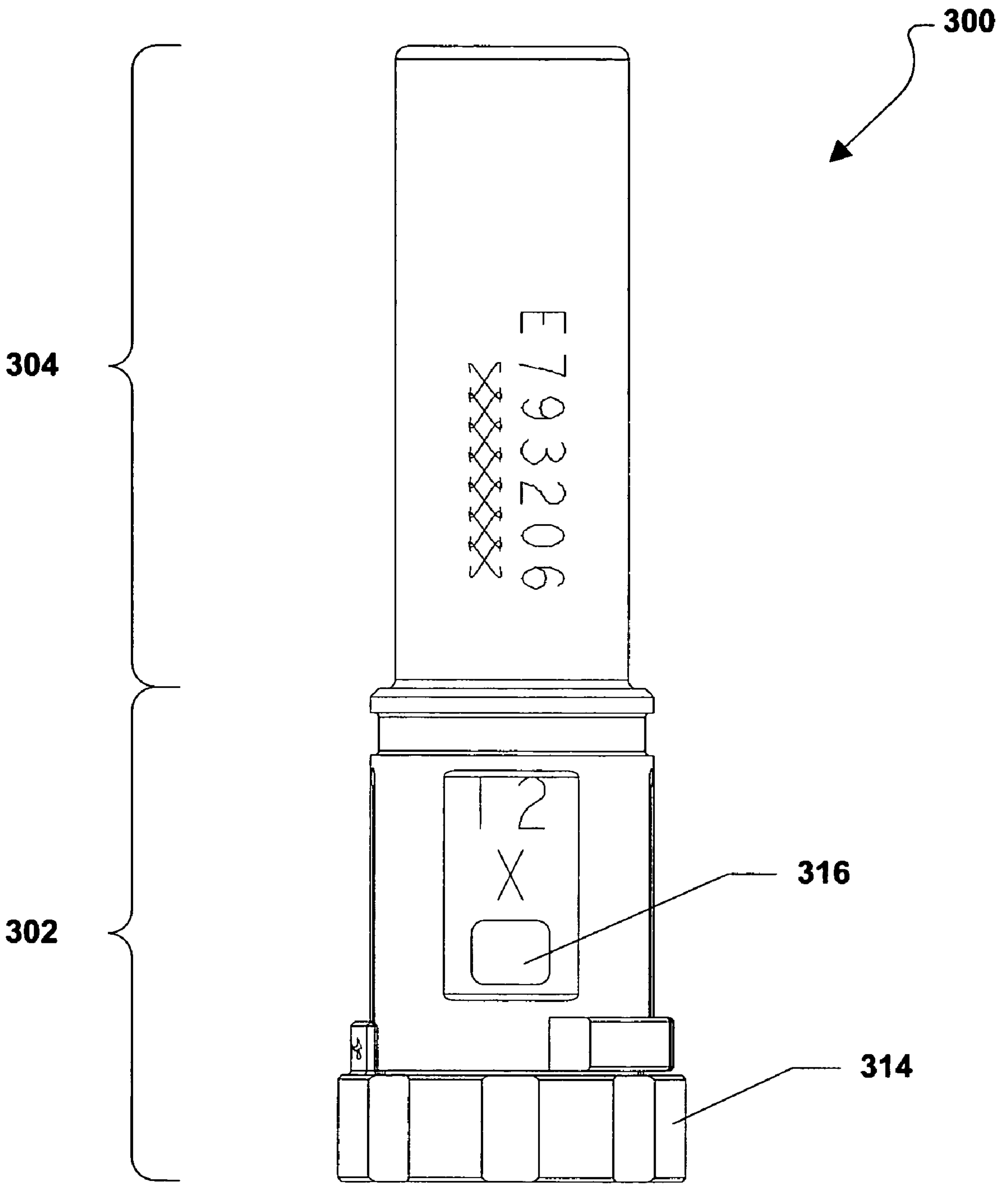
FIG. 6 is another plan view of a drill stop sleeve.

As depicted in FIG. 3 and FIG. 4, the drill bit 200 can include a shank 202 and a body 204 extending therefrom. The body 204 can include a plurality of flutes 206 that can extend helically along the length of the body 204 from the shank 202 to a cutting tip 208. Additionally, the shank 202 can include a first portion 220, a second portion 222 and a third portion 224.

In a particular embodiment, the first portion 220 of the shank 202 can include a hexagonal portion 230 that is sized and shaped to be received within a drill chuck, e.g., a keyed drill chuck, a keyless drill chuck, or any other type of drill chuck well known in the art. Further, the first portion 220 of the shank 202 includes a drill size indicator 232 that is stamped, engraved, or otherwise etched, in the first portion 220 of the shank 202. In a particular embodiment, the drill size indicator 232 is a number that indicates the size of the drill bit in standard units or metric units. Alternatively, the drill size indicator 232 is a number that indicates the size of a screw that is associated with the drill bit, e.g., 5, 6, 8, 10, 12, etc.

FIG. 3 and FIG. 4 illustrate that the second portion 222 of the shank 202 can include a plurality of drill stop grooves 240 that are milled or otherwise formed within the second portion 222 of the shank 202. In a particular embodiment, the drill stop grooves 240 are equally spaced along the second portion 222 of the shank 202. Alternatively, the drill stop grooves 240 are unequally spaced along the second portion 222 of the shank 202. Further, the second portion 222 of the shank 202 includes a plurality of depth indicators 242 that can be stamped, engraved, or otherwise etched within the second portion 222 of the shank 202. The depth indicator 242 can be a number, e.g., 1, 1.25, 1.5, 1.75, 2, etc., that corresponds to a depth, in metric units or standard units, to which the drill bit assembly 100 can be used to drill into bone tissue. Further, the incremental change between the depth indicators can correspond to the spacing between adjacent drill stop grooves 240. For example, if the incremental change between adjacent depth indicators is 0.25 the spacing between adjacent drill stop grooves 240 is 0.25 units, e.g., 0.25 millimeters (0.25 mm).

In a particular embodiment, the drill stop sleeve 300, e.g., an element or elements thereof, can individually engage each of the drill stop grooves 240. Further, when the drill stop sleeve 300 engages one of the plurality of drill stop grooves 240, the drill stop sleeve 300 can be locked in place with respect to the drill stop groove 240. When the drill stop sleeve 300 is locked in place with respect to the drill bit 200, the depth indicator 242 can be aligned with a depth indicator window established within the drill stop sleeve 300, and described in detail below, in order to indicate to the user the maximum depth to which the drill bit assembly 100 can drill into bone tissue. For example, if the depth indicator 242 is six (6) and the units associated with the drill bit assembly 100 are millimeters, the user will know that the drill bit assembly cannot drill into bone tissue any deeper than six millimeters (6 mm).

Referring to FIG. 5 through FIG. 13, the drill stop sleeve 300 is shown. The drill stop sleeve 300 can include a hollow, generally cylindrical first portion 302 and a hollow, generally cylindrical second portion 304. In a particular embodiment, when the drill stop sleeve 300 is installed around the drill bit 200, the first portion 302 of the drill stop sleeve 300 at least partially surrounds the second portion 222 of the shank 202 of the drill bit 200. Further, the second portion 304 of the drill stop sleeve 300 at least partially surrounds the third portion 224 of the shank 202 of the drill bit 200.

As illustrated in FIG. 5 through FIG. 13, the first portion 302 of the drill stop sleeve 300 can include a first locking arm 310 and a second locking arm 312. Further, the drill stop sleeve 300 can include a locking collar 314 and a depth indicator window 316. As described above, each depth indicator 240 of the drill bit 200 can be aligned with the depth indicator window 316 to indicate the maximum depth to which the drill bit assembly 100 can be used to drill into bone tissue.

Figure 13:
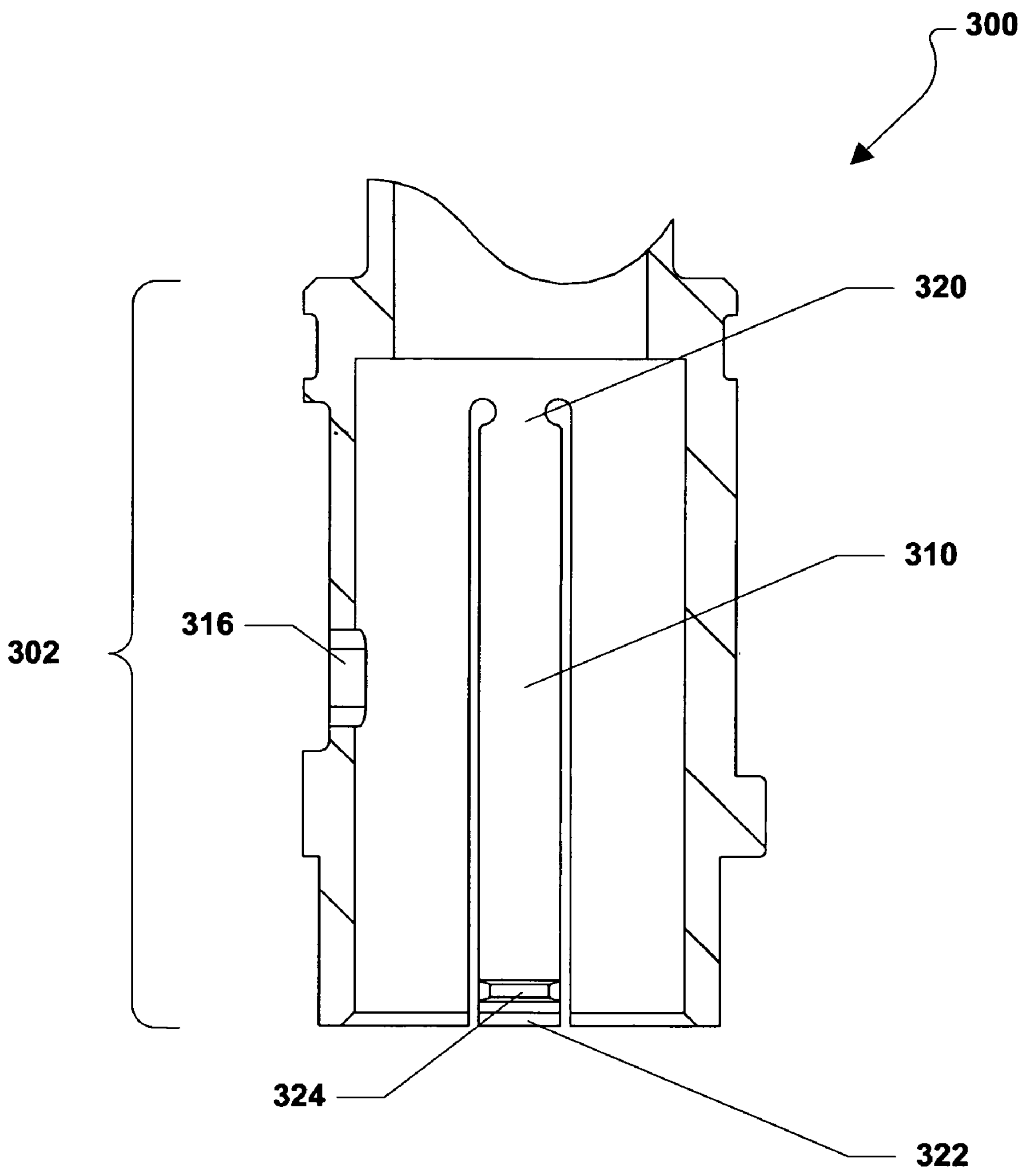
FIG. 13 is another cross-section view of the drill stop sleeve.

As shown in FIG. 13, the first locking arm 310 can include a proximal end 320 and a distal end 322. The proximal end 320 of the first locking arm 310 can be attached to, affixed to, or otherwise integrated with, the first portion 302 of the drill stop 300. Moreover, the distal end 322 of the first locking arm 310 can include a locking tooth 324 than can engage the locking grooves 240 established within the second portion 222 of the shank 202 of the drill bit 200. In a particular embodiment, the second locking arm 312 is configured substantially identical to the first locking arm 3-10.

Figure 7:
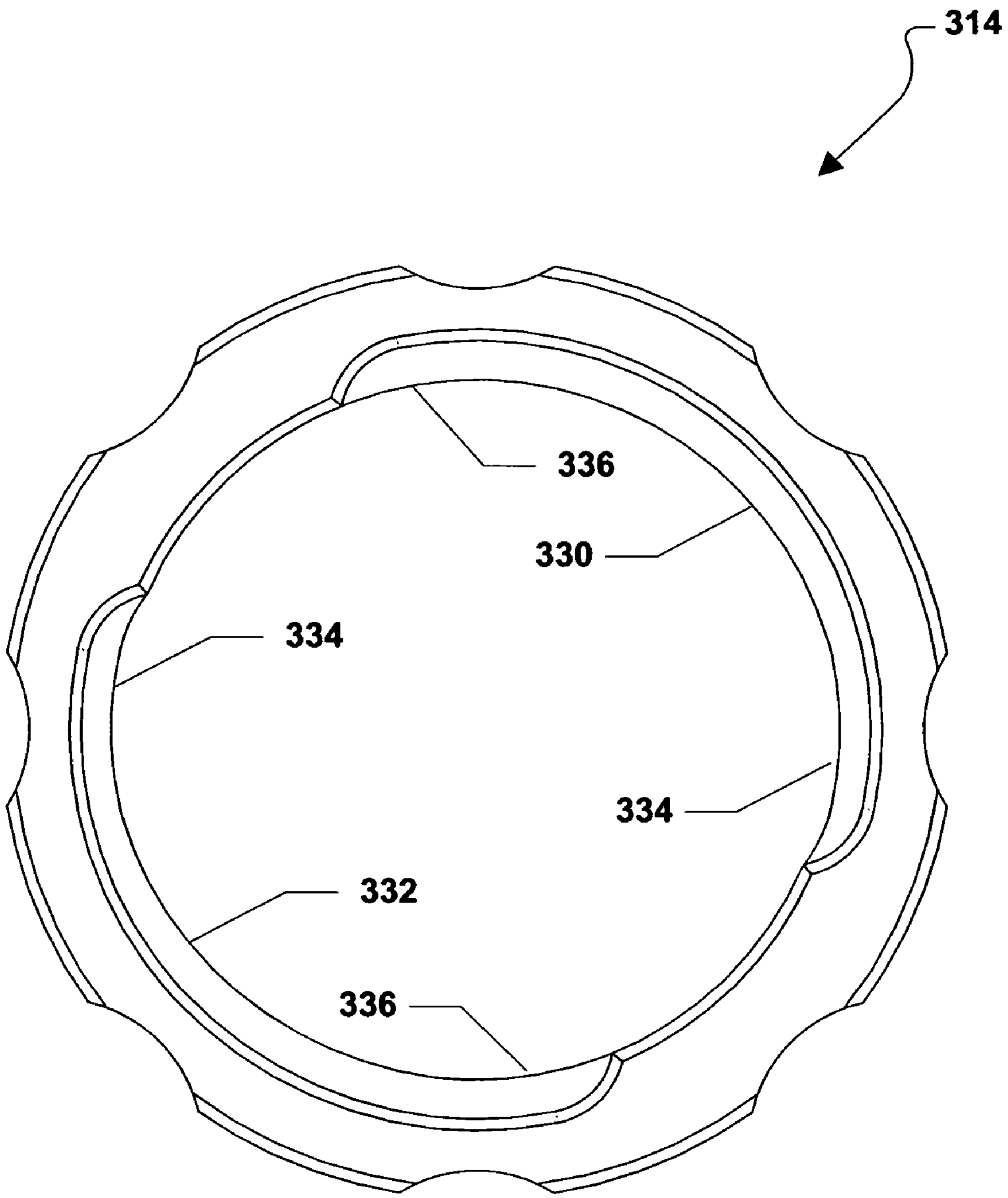
FIG. 7 is plan view of the locking collar.

Referring now to FIG. 7, the locking collar 314 can include an interior perimeter 330 that can include a first locking surface 330 and a second locking surface 332 established therein. Each locking surface 330, 332 can include a leading end 334 and a trailing end 336. In a particular embodiment, a radius of curvature of each locking surface 332, 334 varies along a length of each locking surface 330, 332 from the leading end 334 of each locking surface 330, 332 to the trailing end 336 of each locking surface 330, 332. For example, the radius of curvature decreases from the leading end 334 of each locking surface 330, 332 to the trailing end 336 of each locking surface 330, 332. Accordingly, the curvature of each locking surface 330, 332 increases from the leading end 334 of each locking surface 330, 332 to the trailing end 336 of each locking surface 330, 332.

Figure 8:
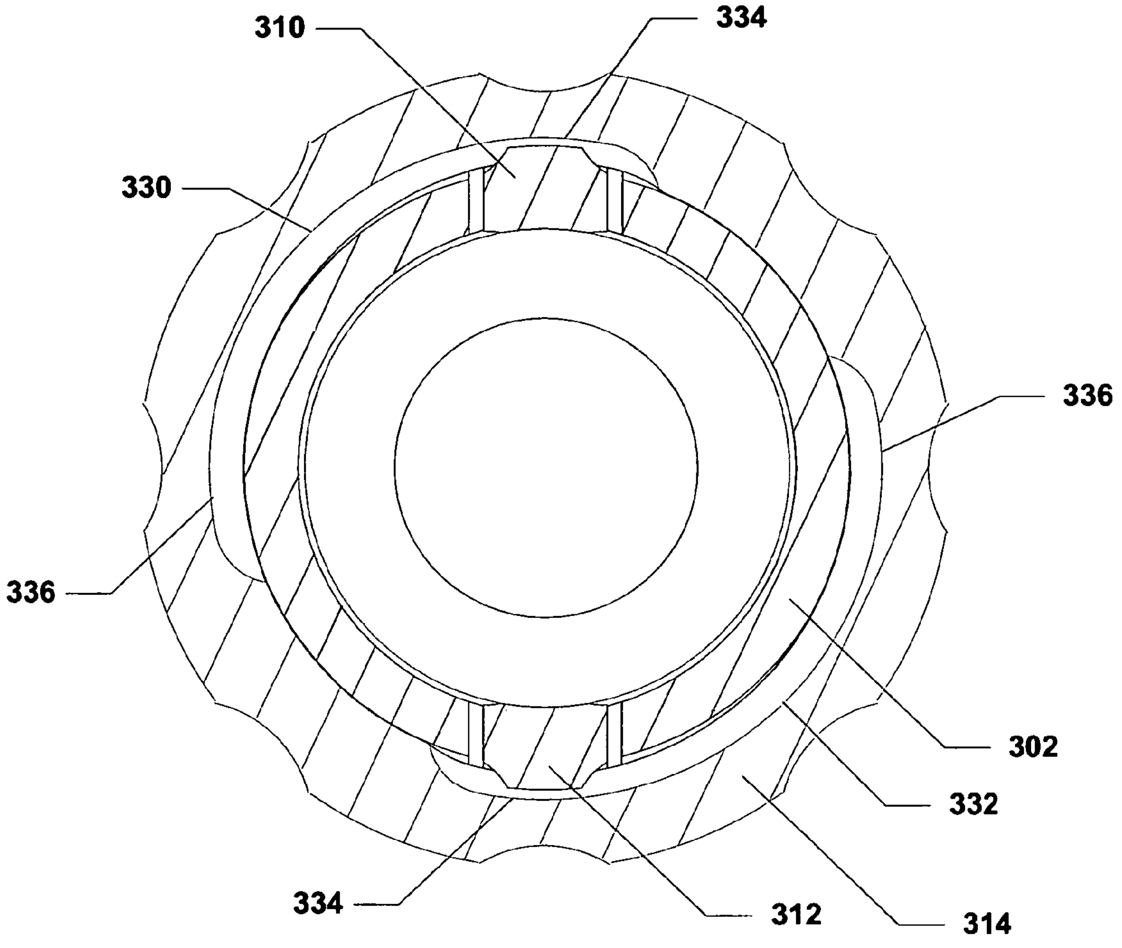
FIG. 8 is a cross-section view of the drill stop sleeve taken along line 8-8 in FIG. 5 with the locking collar rotated into an unlocked position.
Figure 9:
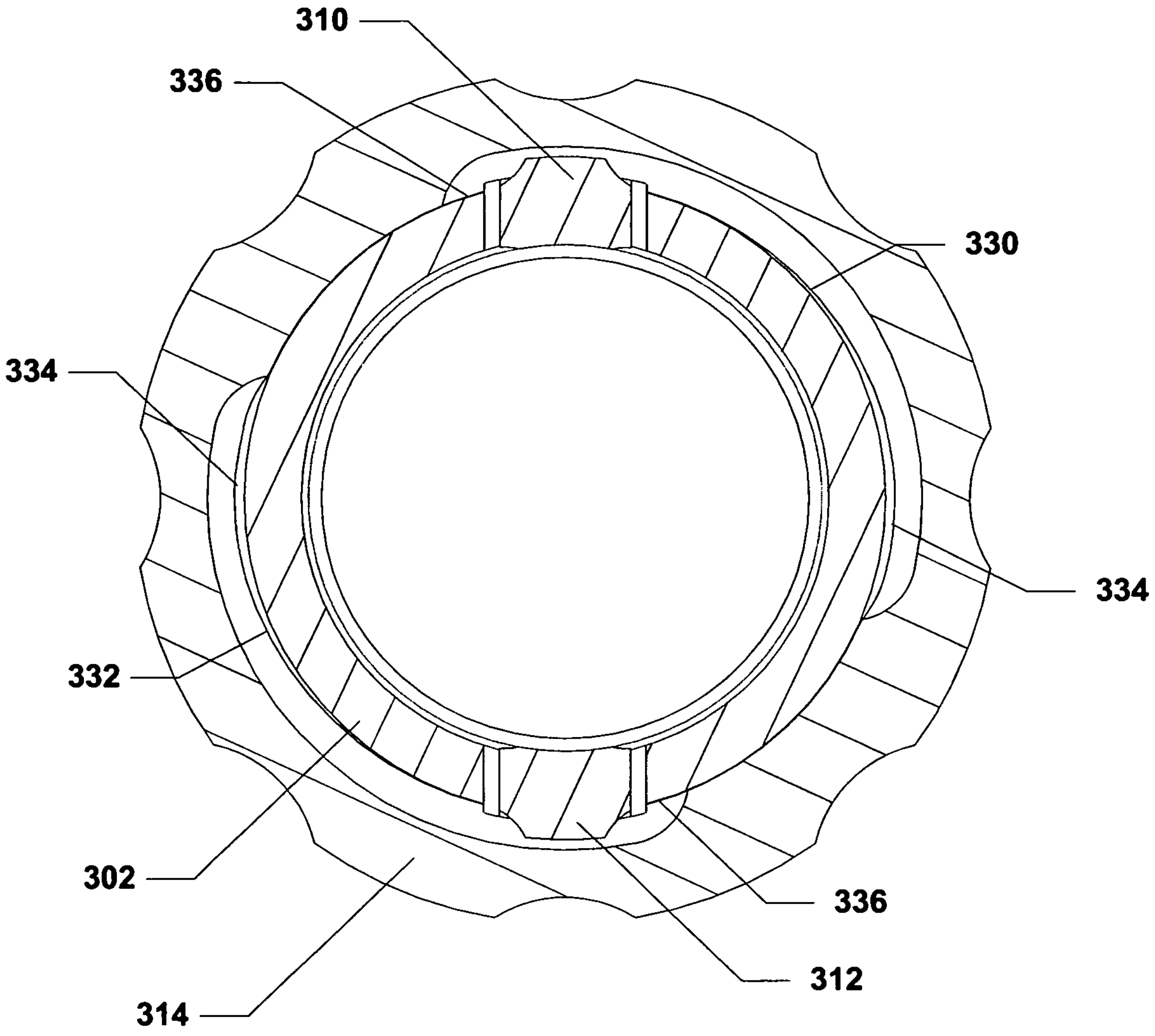
FIG. 9 is another cross-section view of the drill stop sleeve with a locking collar rotated into a locking position.
Figure 10:
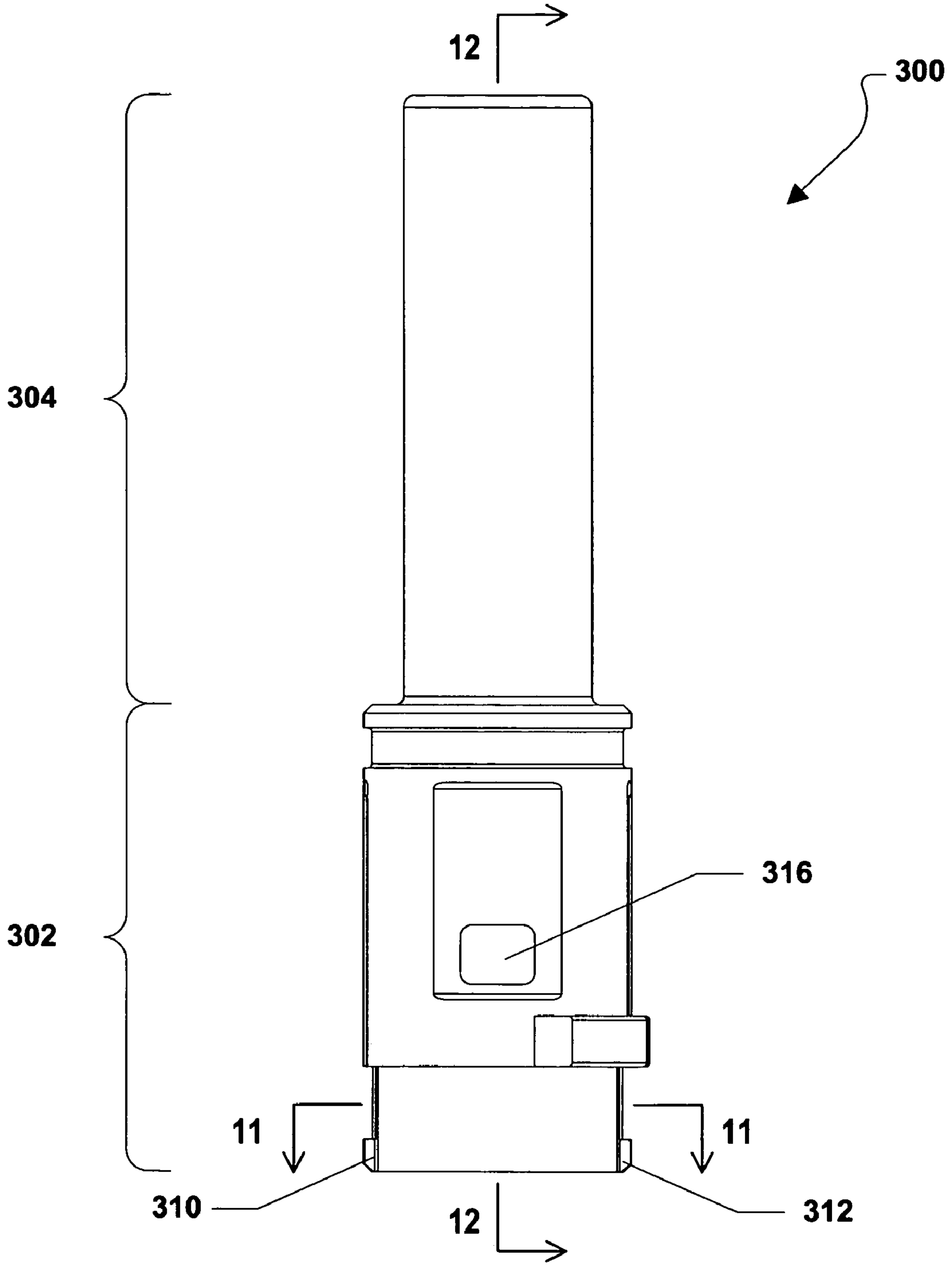
FIG. 10 is a plan view of the drill stop sleeve with the locking collar removed.
Figure 11:
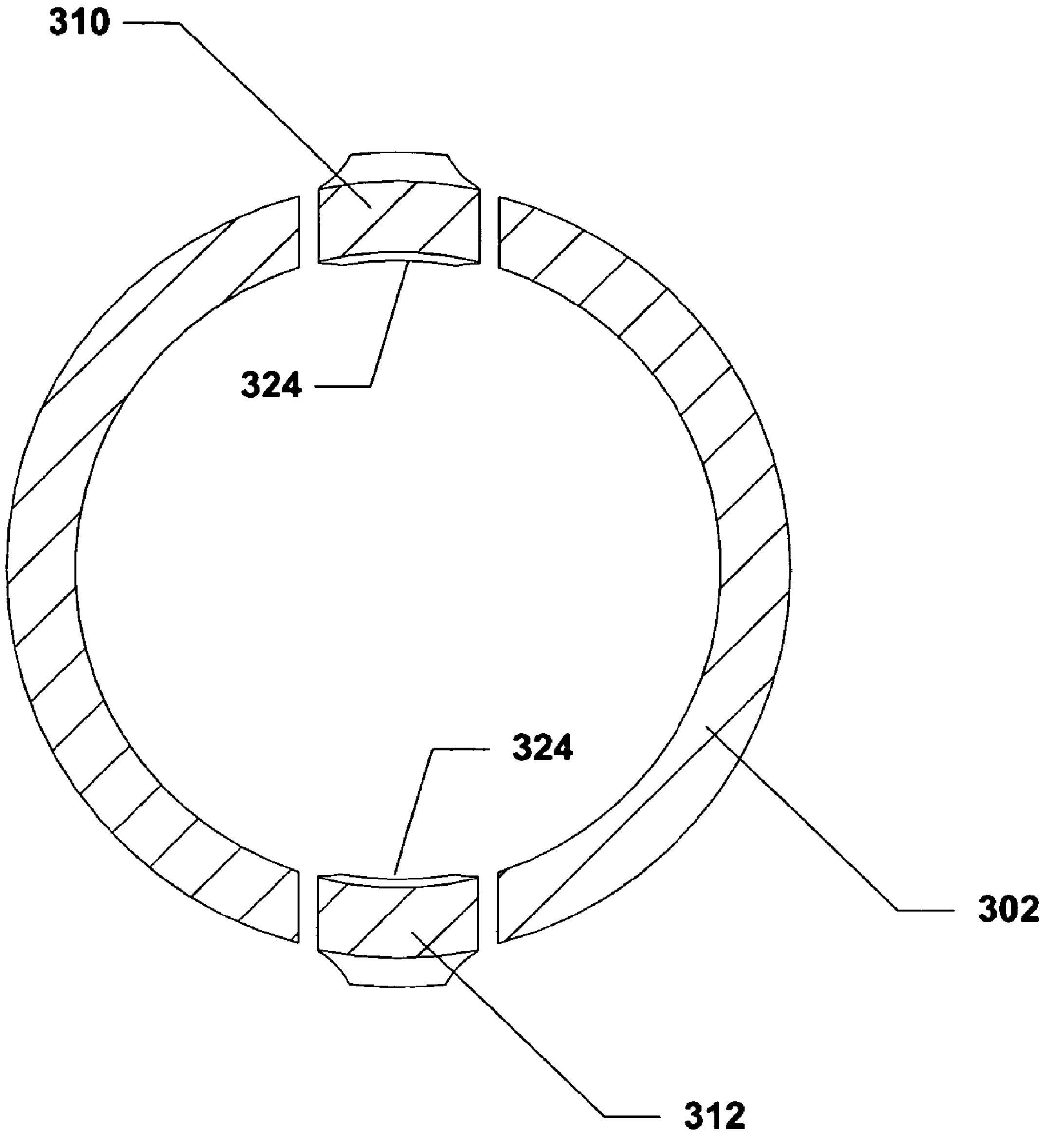
FIG. 11 is a cross-section view of the drill stop sleeve taken along line 11-11 in FIG. 10.
Figure 12:
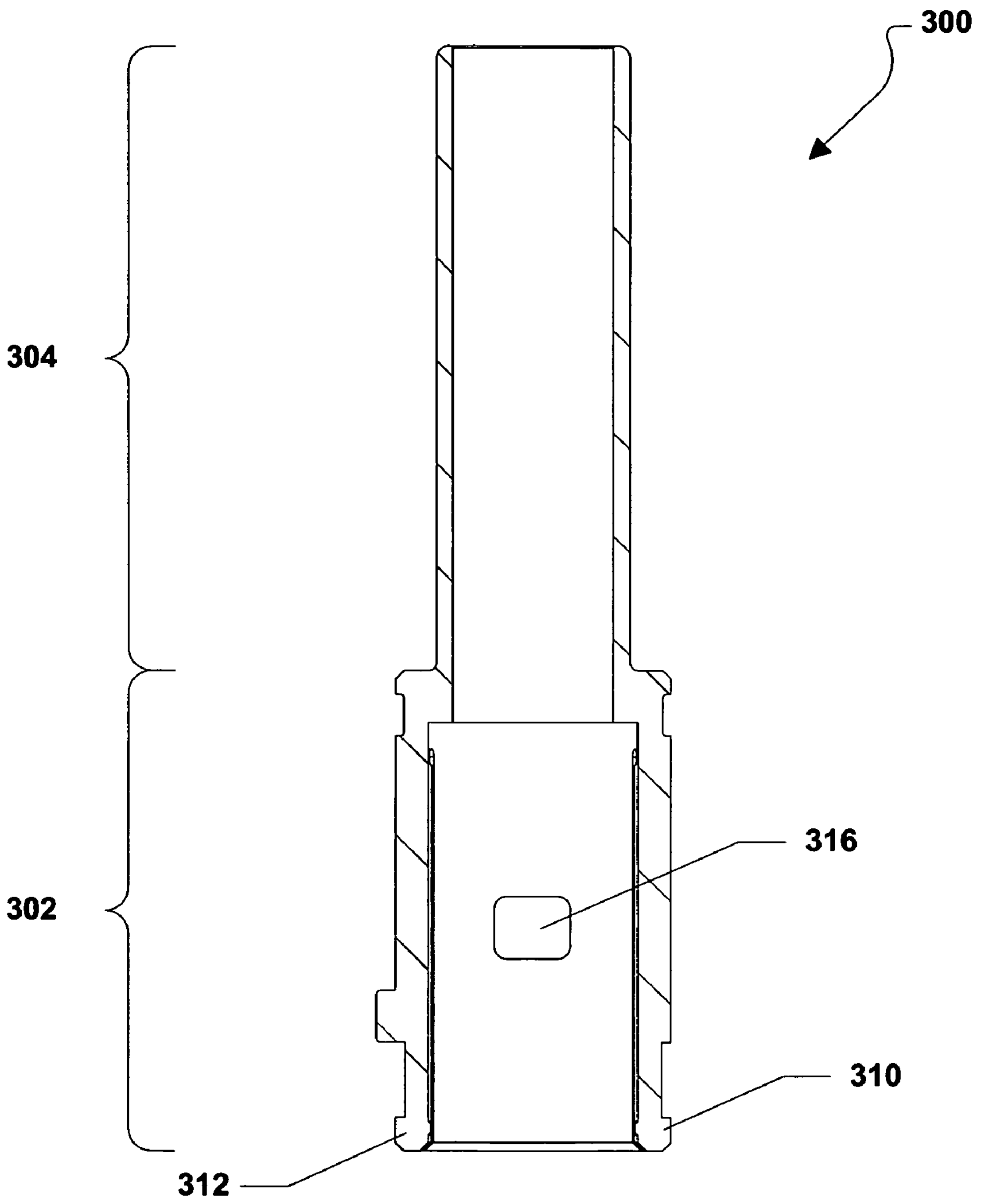
FIG. 12 is a cross section view of the drill stop sleeve taken along line 12-12 in FIG. 10.

FIG. 8 and FIG. 9 illustrate that the locking collar 314 can rotate with respect to the first portion 302 of the drill stop sleeve 300 between an unlocked position, shown in FIG. 8, and a locked position, shown in FIG. 9. In the unlocked position, the leading end 334 of the first locking surface 330 can be substantially aligned with the first locking arm 310 and the leading end 334 of the second locking surface 332 is substantially aligned with the second locking arm 312. In the locked position, the trailing end 336 of the first locking surface 330 can be substantially aligned with the first locking arm 310 and the trailing end 336 of the second locking surface 332 is substantially aligned with the second locking arm 312.

As the locking collar 314 is rotated with respect to the first portion 302 of the drill stop sleeve 300 from the unlocked position to the locked position, the curvature of each locking surface 330, 332 increases. As such, each locking surface 330, 332 can engage a respective locking arm 310, 312 and cause each locking arm 310, 312 to bend, or deflect, slightly inward with respect to the first portion 302 of the drill stop sleeve 300. As each locking arm 310, 312 bends inward, the locking tooth 324 that extends from the distal end 322 of each locking arm 310, 312 can engage one of the plurality of drill stop grooves 240 established within the second portion 222 of the shank 202 of the drill bit 200. Further, when each locking tooth 324 is engaged with a drill stop groove 240, the drill stop sleeve 300 can be locked with respect to the drill bit 200 and the drill stop sleeve 300 can be prevented from moving linearly with respect to the drill bit 200.

Accordingly, a user can slide the drill stop sleeve 300 linearly with respect to the drill bit 200, or slide the drill bit 200 linearly with respect to the drill stop sleeve 300, to a selected drill stop depth and rotate the locking collar 314 from the unlocked position to the locked position in order to lock the drill stop sleeve 300 in place with respect to the drill bit 200. When the drill stop sleeve 300 is locked in place with respect to the drill bit 200, the drill bit assembly 100 cannot be used to drill any deeper into bone tissue than indicated via the depth indicator 232 on the drill bit 200 that can be seen through the depth indicator window 312 on the drill stop sleeve 300.

Figure 14:
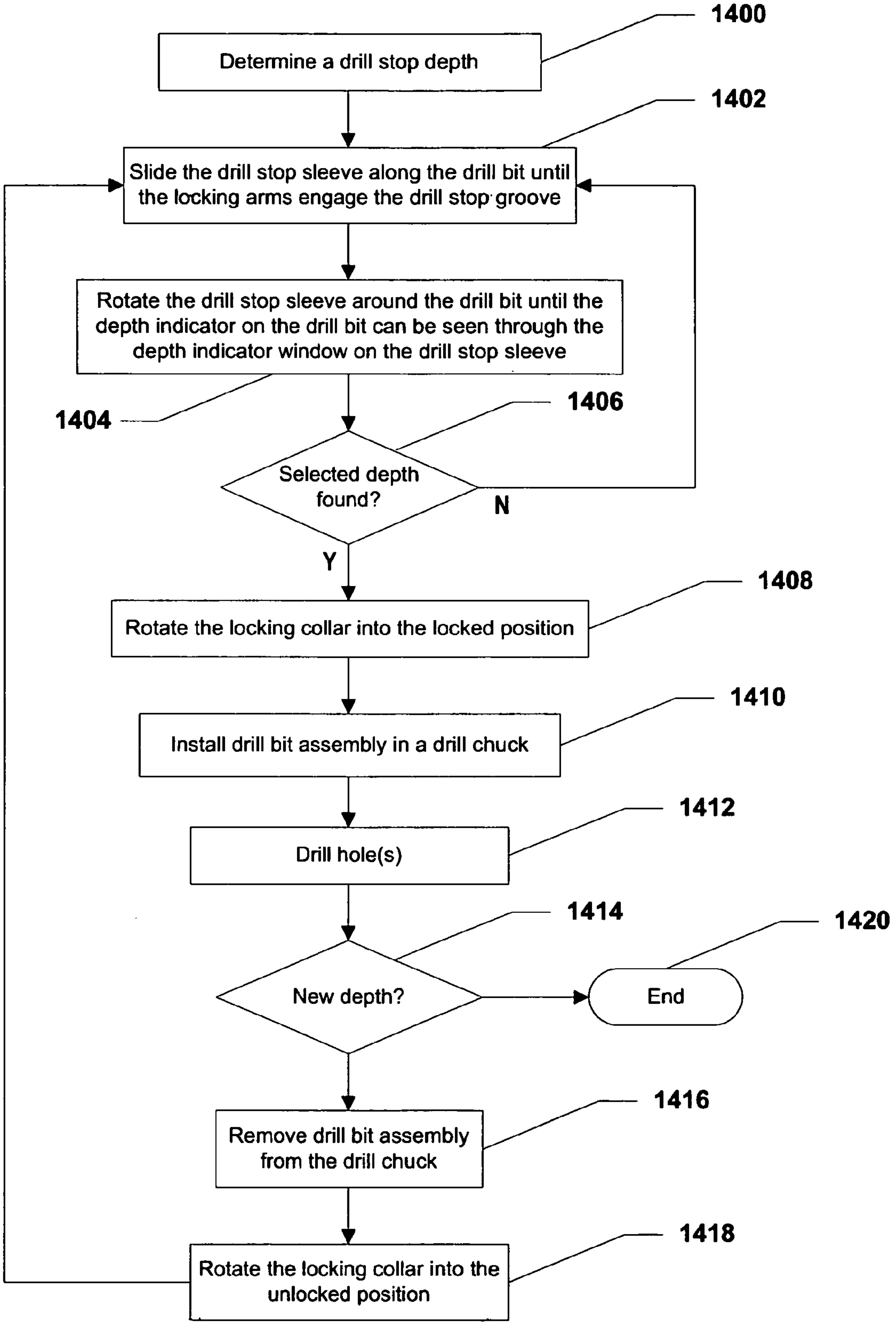
FIG. 14 is a flow chart illustrating a method of using a drill bit assembly.

Referring to FIG. 14, a method of using a drill bit assembly is shown. In a particular embodiment, the drill bit assembly is the drill bit assembly shown and described herein. Commencing at block 1400, a drill stop depth can be determined. In a particular embodiment, the drill stop depth can be determined by a surgeon and correspond to a maximum depth that the surgeon wishes to drill into bone tissue. Moving to block 1402, a drill stop sleeve can be slid along a drill bit until a set of locking arms on the drill stop sleeve engage one of the plurality of drill stop grooves on the drill bit. Further, at block 1404, the drill stop sleeve can be rotated around the drill bit until a depth indicator on the drill bit can be seen through a depth indicator window on the drill stop sleeve.

Proceeding to decision step 1406, it can be determined whether a selected depth is found. In a particular embodiment, the selected depth can be determined by viewing the depth indicator through the depth indicator window. If the selected depth is not found, the method returns to block 1402 and continues as described herein.

Conversely, if the selected depth is found, the method proceeds to block 1408 and a locking collar on the drill stop sleeve can be rotated into a locked position. At block 1410 the drill bit assembly can be installed in a drill chuck of a surgical drill. Further, at block 1412, one or more holes can be drilled using the drill bit assembly. In a particular embodiment, the drill stop sleeve around the drill bit can substantially prevent the drill bit assembly from drilling deeper into bone tissue than the selected drill stop depth.

Continuing to decision step 1414, it can be determined if a new drill stop depth is needed, e.g., to drill one or more holes deeper or shallower than the selected drill stop depth. If a new drill stop depth is necessary, the method proceeds to block 1416 and the drill bit assembly can be removed from the drill chuck of the surgical drill. At block 1418, the locking collar can be rotated into the unlocked position. Thereafter, the method returns to block 1402 and continues as described herein.

Returning to decision step 1414, if a new drill stop depth is not needed, the method can end at state 1420.

With the configuration of structure described above, the drill bit assembly provides a device that can be used to select a drill stop depth. Further, when a drill stop depth is selected a drill stop sleeve can prevent a drill bit from drilling into bone tissue deeper than the selected drill stop depth. Accordingly, when a surgeon selects a particular drilling depth, the surgeon can be confident that drilling beyond the selected depth can be substantially prevented. Further, a drill bit index, i.e., a kit, can be provided that includes a plurality of drill bit assemblies. Each drill bit assembly can include a drill bit having a particular diameter and each drill bit assembly can be adjusted to prevent the drill bit assembly from drilling beyond a selected depth.

In one or more alternative embodiments, the locking collar can be slidably engaged with the drill stop sleeve, e.g., with the first portion of the drill stop sleeve. Further, each locking arm can include an outer ramped surface such that the thickness of each locking arm increases from the proximal end of each locking arm to the distal end of each locking arm. The locking collar can be slid along the first portion of the drill stop sleeve from an unlocked position to a locked position. In the unlocked position the locking collar can be substantially aligned with the proximal ends of the locking arms. Further, in the locked position the locking collar can be substantially aligned with the distal ends of the locking arms. As the locking collar is slid into the locked position, the locking collar can engage the outer ramped surfaces of the locking arms and can cause the locking arms to deflect inward in order to cause the locking teeth to engage one of the plurality of drill stop grooves. Moreover, as the locking collar is slid into the unlocked position, the locking collar can disengage the outer ramped surfaces of the locking arms and can cause the locking arms to deflect outward in order to cause the locking teeth to disengage one of the plurality of drill stop grooves.

The above-disclosed subject matter is to be considered illustrative, and not restrictive, and the appended claims are intended to cover all such modifications, enhancements, and other embodiments that fall within the true spirit and scope of the present invention. For example, it is contemplated that the drill bit assembly shown and described herein can find utility in non-surgical applications not described in detail herein. Thus, to the maximum extent allowed by law, the scope of the present invention is to be determined by the broadest permissible interpretation of the following claims and their equivalents, and shall not be restricted or limited by the foregoing detailed description.

What is claimed is:

1. A drill bit assembly, comprising:

a drill bit comprising a plurality of drill stop grooves established therein; and a drill stop sleeve having a hollow cylinder configuration wherein the drill bit is placed therethrough, the drill stop sleeve comprising a locking collar and a locking arm, the locking arm having a proximal end and a distal end wherein the thickness of the locking arm increases from the proximal end to the distal end, wherein the locking collar is movable in a linear direction on the drill stop sleeve between an unlocked position in which the drill stop sleeve is movable along the drill bit to one of a plurality of drill stop depths and a locked position in which the drill stop sleeve is locked along the drill bit in one of the plurality of drill stop depths; and wherein the locking arm is configured to engage one of the plurality of drill stop grooves when the locking collar is in the locked position.

2. The drill bit assembly of claim 1, wherein the drill stop sleeve substantially prevents the drill bit from drilling beyond one of a plurality of drill stop depths when the locking collar is in the locked position.

3. The drill bit assembly of claim 2, wherein the drill stop sleeve selectively engages each of the plurality of drill stop grooves.

4. The drill bit assembly of claim 3, wherein each drill stop groove corresponds to a drill stop depth.

5. The drill bit assembly of claim 4, wherein the drill bit comprises a shank and a body and the plurality of drill stop grooves are established along the shank.

6. The drill bit assembly of claim 5, wherein the plurality of drill stop grooves are equally spaced along the shank.

7. The drill bit assembly of claim 2, wherein the drill bit further comprises a plurality of depth indicators wherein each of the depth indicators corresponds to one of the plurality of drill stop depths.

8. The drill bit assembly of claim 7, wherein the drill stop sleeve further comprises a depth indicator window through which one of the plurality of depth indictors can be seen.

9. The drill bit assembly of claim 1, wherein the locking arm comprises a locking tooth wherein the locking tooth engages one of the plurality of drill stop grooves when the locking collar is in the locked position.

10. The drill bit assembly of claim 9, wherein the locking collar comprises a locking surface wherein the locking surface deflects the locking arm as the locking collar slidably engages the locking arm.

11. A drill stop sleeve configured to be positioned around a corresponding drill bit, the drill stop sleeve comprising:

a hollow cylinder configuration wherein the corresponding drill bit is placed therethrough;

a locking arm having a proximal end and a distal end wherein the thickness of the locking arm increases from the proximal end to the distal end, the locking arm configured to engage one of a plurality of drill stop grooves established within the corresponding drill bit; and a locking collar movable in a linear direction on the drill stop sleeve between an unlocked position in which the locking arm does not engage one of the plurality of drill stop grooves and a locked position in which the locking arm engages one of the plurality of the drill stop grooves.

12. A method of drilling a hole in an item, the method comprising:

providing a drill bit assembly comprising a drill bit that includes a plurality of drill stop grooves established therein and a drill stop sleeve having a hollow cylinder configuration wherein the drill bit is placed therethrough;

selecting a drill stop depth on a drill bit assembly; and locking a drill stop sleeve with respect to a drill bit, wherein the drill stop sleeve includes a locking collar and a locking arm having a proximal end and a distal end wherein the thickness of the locking arm increases from the proximal end to the distal end, wherein the locking collar is movable in a linear direction on the drill stop sleeve between an unlocked position and a locked position, and wherein the locking arm is configured to engage one of the plurality of drill stop grooves when the locking collar is in the locked position to substantially prevent the drill bit from drilling deeper into the item than a selected drill stop depth.

13. A kit for field use, the kit comprising:

a drill bit assembly comprising:

a drill bit comprising a plurality of drill stop grooves established therein; and a drill stop sleeve having a hollow cylinder configuration wherein the drill bit is placed therethrough, the drill stop sleeve comprising a locking collar movable in a linear direction on the drill stop sleeve between an unlocked position in which the drill stop sleeve is movable along the drill bit to one of a plurality of predetermined drill stop depths and a locked position in which the drill stop sleeve is locked along the drill bit in one of the plurality of predetermined drill stop depths; and a locking arm having a proximal end and a distal end wherein the thickness of the locking arm increases from the proximal end to the distal end the locking arm configured to engage one of the plurality of drill stop grooves when the locking collar is in the locked position; and instructions for drilling a hole with the drill bit assembly.

* * * * *